United States Patent [19]
Nishimoto et al.

[11] Patent Number: 5,858,992
[45] Date of Patent: Jan. 12, 1999

[54] NON-REDUCING SACCHARIDES, THEIR PREPARATION AND USE

[75] Inventors: Tomoyuki Nishimoto; Hiroto Chaen; Toshiyuki Sugimoto; Toshio Miyake, all of Okayama, Japan

[73] Assignee: Kabushiki Kaisha Hayashibara Seibutsu Kagaku Kenkyujo, Okayama, Japan

[21] Appl. No.: 962,880

[22] Filed: Nov. 4, 1997

Related U.S. Application Data

[63] Continuation-in-part of Ser. No. 594,454, Jan. 31, 1996, abandoned.

[30] Foreign Application Priority Data

Feb. 10, 1995 [JP] Japan .................................... 7-044985
Feb. 10, 1995 [JP] Japan .................................... 7-044996
Feb. 10, 1995 [JP] Japan .................................... 7-045054

[51] Int. Cl.$^6$ ........................ A61K 31/715; A01N 43/04; C07H 1/00
[52] U.S. Cl. ........................ 514/54; 514/53; 536/123.12; 536/123.1
[58] Field of Search .................. 514/54, 53; 536/123.12, 536/123.1

[56] References Cited

U.S. PATENT DOCUMENTS

| | | | |
|---|---|---|---|
| 4,518,581 | 5/1985 | Miyake et al. | 424/48 |
| 4,521,252 | 6/1985 | Miyake et al. | 127/46.3 |

FOREIGN PATENT DOCUMENTS

| | | |
|---|---|---|
| 0 480 640 | 4/1992 | European Pat. Off. . |
| 0 606 753 A2 | 12/1993 | European Pat. Off. . |
| 0 628 630 A2 | 4/1994 | European Pat. Off. . |
| 0 636 632 | 2/1995 | European Pat. Off. . |
| 0 636 693 | 2/1995 | European Pat. Off. . |
| 0 622 479 | 7/1995 | European Pat. Off. . |
| 62-50477 | 10/1987 | Japan . |
| 63-240758 | 10/1988 | Japan . |
| 4-50319 | 8/1992 | Japan . |
| 5-39584 | 6/1993 | Japan . |
| 7-213283 | 8/1993 | Japan . |

OTHER PUBLICATIONS

Mitsuoka, A Color Atlas of Anaerobic Bacteria, Inst. Of Phys. Chem. Res., pp. 55–65 (1984).

Takeuchi, Studies on the Less–Fermentable Sugars which Inhibit the Insoluble Glucan Synthesis by Streptococcus Mutans, Jpn. J. Oral Biol., vol. 26, pp. 698–713, 1984.

Bradbury et al, Determination of the Structures of Trisaccharides by $^{13}$C–N.M.R. Spectroscopy, vol. 126, pp. 125–156, 1984.

Ajisaka et al, Regioselective Syntheses of Trehalose–Containing Trisaccharides Using Various Glycohydrolases, Carbohydrate Research, vol. 199, pp. 227–234, 1990.

Institute for Fermaentation, Osaka IFO, List of Cultures, Micoorganisms, Ninth Edition, 1992.

Gherna et al, Catalogue of BActeria and Phages, American Type Culture Collection, No. 33923, Eighteenth Edition, 1992.

Okada et al, Digestion and Fermentation of Pullulan, National Institute of Nutrtion, vol. 43 No. 1, pp. 23–29, 1990.

Yazawa et al, Oligosaccharides and Polysaccharides Specificalllly Utilizable by Bifidobacteria, Chem. Pharm. Bull., vol. 26, pp. 3306–3311, 1978.

S. Koto et al., "Alpha–D–Glucosylation by 6–0–Acetyl–2, 3,4–Tri–O–Benzyl–D–Glucopyranose Using Trimethylsilyl Triflate and Pyridine", Bull. Chem. Soc. Japan, vol. 59, 1986, pp. 411–414.

*Primary Examiner*—John Kight
*Assistant Examiner*—Everett White
*Attorney, Agent, or Firm*—Browdy and Neimark

[57] ABSTRACT

α-Isomaltosyl α-isomaltoside represented by O-α-D-glucopyranosyl -(1→6)-α-D-glucopyranosyl O-α-D-glucopyranosyl-(1→6) -α-D-glucopyranoside is a novel non-reducing saccharide which promotes the growth of bifid bacteria, has an anti-caries activity, and promotes the mineral absorption. Similarly as the non-reducing saccharide, α-isomaltosyl α-glucoside and α-isomaltotriosyl α-glucoside can be also used to prevent caries and promote the growth of bifid bacteria and the mineral absorption. These saccharides can be used alone or in combination in a variety of foods, cosmetics and pharmaceuticals.

12 Claims, 3 Drawing Sheets

NON-REDUCING SACCHARIDES, THEIR PREPARATION AND USE

This application is a continuation-in-part of U.S. application Ser. No. 08/594,454, filed Jan. 31, 1996, now abandoned.

BACKGROUND OF THE INVENTION

1. Field of the Invention

The present invention relates to a novel non-reducing saccharide, i.e. α-isomaltosyl α-isomaltoside (O-α-D-glucopyranosyl -(1→6)-α-D-glucopyranosyl-O-α-D-glucopyranosyl-(1→6) -α-D-glucopyranoside), its preparation and uses. Furthermore, the present invention relates to a composition which contains as an effective ingredient one or more of the novel saccharide and conventionally known α-isomaltosyl α-glucoside and α-isomaltotriosyl α-glucoside, their preparations and uses.

2. Description of the Prior Art

Trehalose or α,α-trehalose is a non-reducing disaccharide consisting of glucose residues and is widely distributed in natural kingdom: For example, trehalose is present in fungi, yeasts, bacteria, mushrooms, higher plants, insects, etc., although the amount is relatively low. Because of its non-reducibility, trehalose neither reacts with substances having amino acid residues such as amino acids and proteins nor causes the Maillard reaction or the amino carbonyl reaction. Therefore, trehalose does not deteriorate amino acid-containing substances. In addition, it is a stable substance and can be freely used and processed without fear of causing browning and deterioration. Thus, trehalose has been expected to be used in a variety of fields. For example, Japanese Patent Laid-Open No.240,758/88 discloses that trehalose is a growth-promoting saccharide for bifid bacteria and is relatively low in cariogenicity. The following researches revealed that trehalose is superior to sucrose on these activities, but the levels of which are relatively low. Therefore, the development of saccharides with higher superiority has been in great demand.

As disclosed in "*Chemical & Pharmaceutical Bulletin*", Vol.26, pp.3,306–3,311(1978), isomaltooligosaccharides such as isomaltotriose alias dextrantriose, and isomaltotetraose alias dextrantetraose, etc., are known as growth-promoting saccharides for bifid bacteria, and as disclosed in Japanese Patent Publication Nos.39,584/93 and 53,465/93, trehalose is known as a substantially non- or anti-cariogenic saccharide.

However, isomaltooligosaccharides have a reducing activity and readily react with amino acids to cause a browning reaction which deteriorates food products during their preparations. Therefore, the development of superior saccharides has been greatly demanded.

The present inventors concentrated on these properties of trehalose and isomaltooligosaccharides and started to screen saccharides which have an insubstantial reducibility, a selective growth activity for bifid bacteria, and an anti-cariogenicity while expecting greatly the existence of such saccharides among oligosaccharides having trehalose- and isomaltose-structures. As regards such oligosaccharides, Katsumi AJISAKA and Hiroshi FUJIMOTO reported in "*Carbohydrate Research*", Vol.199, pp.227–234(1990) that the condensation reaction between trehalose and glucose using α-glucosidase from a microorganism of the species Saccharomyces sp. or glucoamylase from a microorganism of the species Rhizopus niveus forms α-isomaltosyl α-glucoside represented by O-α-D-glucopyranosyl-(1→6) -α-D-glucopyranosyl α-D-glucopyranoside. While Kin et al. reported in "*Journal of the Japanese Society of Starch Science*", Vol.40, No.3, page 349(1993) that a saccharide-transferring reaction between dextran and trehalose using isomaltodextranase from *Arthrobacter globiformis* T6 strain forms α-isomaltosy α-glucoside represented by O-α-D-glucopyranosyl-(1→6)-O-α-D-glucopyranosyl -(1→6)-α-D-glucopyranosyl α-D-glucopyranoside. However, the present inventors noticed that these reports disclose no characteristic property of these saccharides as they need and there has been no report of saccharides having both trehalose- and isomaltose-structures.

SUMMARY OF THE INVENTION

To overcome the aforesaid object, the present inventors energetically continued studying such saccharides, compositions and preparations.

As a result, the inventors found that non-reducing oligosaccharides such as α-isomaltosyl α-glucoside, α-isomaltosyl α-isomaltoside, and α-isomaltotriosyl α-glucoside (hereinafter may be referred to as "SACCHARIDES") have a satisfactory stability, a high growth promoting activity for bifid bacteria, and an anti-caries activity, and have established a growth-promoting agent for bifid bacteria and an anti-caries agent, which contain one or more of SACCHARIDES as an effective ingredient, their preparations and uses.

BRIEF DESCRIPTION OF THE ACCOMPANYING DRAWINGS

DETAILED DESCRIPTION OF THE INVENTION

Figure 1:
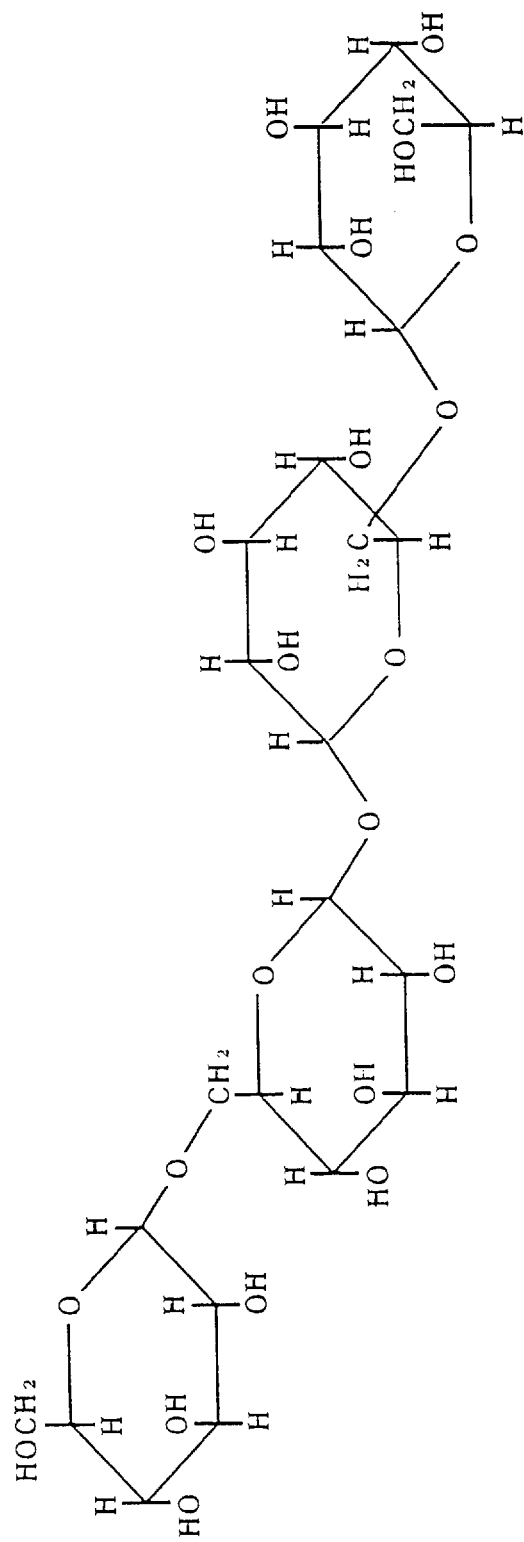
FIG. 1 is a figure of the structure of α-isomaltosyl α-isomaltoside.

The present invention is to establish a novel non-reducing saccharide having both trehalose- and isomaltose-structures within the molecule, i.e. α-isomaltosyl α-isomaltoside, its preparation and uses. Furthermore, the present invention is to establish compositions, particularly, a growth-promoting agent for bifid bacteria and an anti-caries agent, which contain as an effective ingredient the novel non-reducing saccharide, its preparation and uses. The present inventors also found that conventionally known α-isomaltosyl α-glucoside and α-isomaltotriosyl α-glucoside can be used for such purposes similarly as α-isomaltosyl α-isomaltoside.

Although the α-isomaltosyl α-glucoside, α-isomaltosyl α-isomaltoside, and α-isomaltotriosyl α-glucoside used in the present invention can be chemically synthesized, they can be advantageously prepared on an industrial scale by biochemical reactions, particularly, can be prepared by allowing α-glucosidase (EC 3.2.1.20) to act on aqueous solutions containing trehalose and amylaceous substances.

Any aqueous solution containing trehalose and an amylaceous substance(s) can be used in the present invention as long as α-glucosidase produces SACCHARIDES when acts on the solution. For example, aqueous solutions containing free trehalose and amylaceous substances, and other aqueous solutions containing compounds having trehalose structures and amylaceous structures of α-1,4 glucosidic linkages within their molecules can be arbitrarily used.

In the case of using aqueous solutions containing free trehalose and amylaceous substances, commercially available trehalose and, if necessary, other trehalose preparations prepared by extracting from yeasts by conventional method, separating from cultures of microorganisms capable of producing trehalose, or allowing enzymes to act on the later described amylaceous substances can be used in the present invention. While starches and their partial hydrolysates such as gelatinized-, liquefied- and solubilized-starches and maltooligosaccharides can be used as the free amylaceous substances. The partial starch hydrolysates can be readily prepared by allowing to act on starches liquefying enzymes such as α-amylases and starch debranching enzymes such as pullulanase and isoamylase.

The methods to simultaneously produce trehalose and amylaceous substances include, for example, those as disclosed in Japanese Patent Application Nos.156,33893 and 79,29194 applied by the present applicant, where a non-reducing saccharide-forming enzyme and a trehalose-releasing enzyme are allowed to act on aqueous solutions containing amylaceous substances, and those as disclosed in Japanese Patent Application Nos.199,97193 and 144,09294 applied by the present applicant, where a maltosetrehalose converting enzyme is allowed to act on aqueous solutions containing maltose.

In the case of using compounds having trehalose structures and amylaceous structures of α-1,4 glucosidic linkages, these compounds can be prepared, for example, as disclosed in European Patent Publication No.0606753 A2 applied by the present applicant, by allowing a non-reducing saccharide-forming enzyme to act on aqueous solutions containing amylaceous substances to form compounds having amylaceous structures of α-1,4 glucosidic linkages and having a trehalose structure as an end unit, and, as disclosed in Japanese Patent Application Nos.178,62393 and 167, 48694 applied by the present applicant, by allowing a non-reducing saccharide-forming enzyme and cyclomaltodextrin glucanotransferase to act on aqueous solutions containing amylaceous substances to form compounds having trehalose structures and amylaceous structures of α-1,4 glucosidic linkages within their molecules.

Any α-glucosidase can be used in the present invention as long as it can convert α-1,4 glucosidic linkages in amylaceous substances into α-1,6 glucosidic linkages: For example, those derived from microorganisms such as *Aspergillus niger, Aspergillus awamori, Aspergillus saitoi, Mucor javanicus, Penicillium crysogenum, Candida tropicalis*, etc., can be suitably used.

The enzymatic reaction conditions and methods used in the present invention are those which can form SACCHARIDES. Usually, aqueous solutions containing trehalose and amylaceous substances are treated with at least 0.1 unit/g starch, on a dry solid basis (d.s.b.), preferably, 1–100 units/g of starch, d.s.b., of α-glucosidase at a temperature of 20°–80° C. and a pH of 3–9 for about 0.1–100 hours, preferably, about 1–70 hours. In the present invention, one unit activity of α-glucosidase is defined as the amount that forms 2 μmoles of glucose per min when allowed to act on 0.2 w/v % maltose as a substrate at 40° C. and pH 5.5. The enzymatic reaction forms SACCHARIDES and oligosaccharides where one or several α-glucosyl residues are linked to the SACCHARIDES in an α-1,6 glucosidic linkage such as α-isomaltotriosyl α-isomaltoside, α-isomaltotetraosyl α-isomaltoside, and α-isomaltotriosyl α-isomaltrioside. The reaction mixtures thus obtained usually contain reducing saccharides such as glucose, maltose and maltotriose, as well as intact trehalose and amylaceous substances. Glucoamylase forms mainly α-isomaltosyl α-glucoside and α-isomaltosyl α-isomaltoside as a non-reducing saccharide when allowed to act on the reaction mixtures, and the accumulations are collected and used in the present invention.

Usually, the solutions, containing SACCHARIDES produced by the above enzymatic reactions, contain 5–40 w/w %, d.s.b., of non-reducing oligosaccharides having trehalose- and isomaltose-structures (the symbol "w/w %" is abbreviated as "%" in the present specification, if not specified otherwise) wherein the contents of α-isomaltosyl α-isomaltoside and α-isomaltosyl α-glucoside are 1–5% and 5–30%, d.s.b. The solutions can be filtered and purified into liquid products which, if necessary, can be further concentrated into syrups or dried into solids.

To improve the property of SACCHARIDES, they may be separated and purified into higher purity SACCHARIDES before use. As the methods for such a purpose, fermentation methods using yeasts, membrane filtration methods, fractional precipitation methods, alkali-treating methods, and column chromatographies can be suitably used to separate and remove concomitant saccharides. Particularly, the column chromatographies using strong-acid cation exchangers as disclosed in Japanese Patent Publication Nos.50,47787 and 50,31992 can be arbitrarily used to remove concomitant saccharides into fractions rich in SACCHARIDES. In such cases, any one of fixed bed, moving bed, and quasi-moving bed methods can be freely used.

If necessary, SACCHARIDES with an insubstantial reducibility can be arbitrarily obtained by hydrogenating in usual manner saccharide mixtures containing SACCHARIDES to convert the concomitant reducing saccharides such as glucose and maltose into sugar alcohols to lose their reducing power.

SACCHARIDES in themselves have substantially no reducibility but have a satisfactory stability, a relatively low sweetening power, a relatively high quality, and a mild sweetness. They are not readily digested in the digestive tracts when administered orally to animals including human and mostly transferred to their large intestines and effectively used as a growth-promoting agent for bifid bacteria. The selective growth for bifid bacteria results in the formation of organic acids such as acetic acid and lactic acid, as well as in the intestinal pH reduction and the growth inhibition of harmful microorganisms such as putrefactive bacteria and other microorganisms causative of spontaneous infectious diseases. Furthermore, SACCHARIDES inhibit the formation of harmful substances such as ammonia, indole and cresol, adequately stimulate the intestines, and appropriately promotes the peristalsis to control the intestinal conditions. SACCHARIDES, capable of promoting the growth of bifid bacteria, are utilized to form organic acids in the large intestines, followed by lowering the intestinal pH level, increasing the solubility, and the absorption of minerals such as calcium, iron and zinc susceptible to deficiency. Therefore, SACCHARIDES can be arbitrarily used as an agent for promoting mineral absorption. In addition, they are not readily fermented by dental caries-inducing microorganisms and inhibit the formation of insoluble glucans from sucrose by such microorganisms, resulting in the reduction of plaque formation. Because of these, SACCHARIDES can be arbitrarily used as a sweetener, substantially free from dental caries inducibility and used as an anti-caries agent. Furthermore, SACCHARIDES have a satisfactory chemical stability, stabilize amino acids, oligopeptides susceptible to the browning reaction with other saccharides, and biologically active substances susceptible to loss of their effective ingredients and activities, and have properties of an osmotic-pressure controlling activity, body-imparting activity, gloss-imparting activity, moisture-retaining activity, viscosity-imparting activity, crystallization-preventing activity, insubstantial fermentability, and starch retrogradation-preventing activity.

These satisfactory properties of SACCHARIDES are suitably used in a variety of compositions, which have a growth-promoting activity for bifid bacteria and an anti-caries activity, in the form of food products, feeds, pet foods, and pharmaceuticals. Particularly, the present effective ingredients can be arbitrarily incorporated into one or more compounds selected from sugar alcohols, minerals and sucrose to obtain compositions with a growth promoting activity for bifid bacteria and an anti-caries activity.

Crude or purified SACCHARIDES can be used intact as a seasoning for sweetening. If necessary, these SACCHARIDES can be used along with one or more other sweeteners such as powdered syrup, glucose, maltose, trehalose, sucrose, lactosucrose, isomerized sugar, honey, maple sugar, sorbitol, maltitol, lactitol, dihydrochalcone, stevioside, α-glycosyl stevioside, rebaudioside, glycyrrhizin, L-aspartyl L-phenylalanine methyl ester, saccharin, glycine and alanine; and/or with a filler such as dextrin, starch or lactose.

The SACCHARIDES can be used intact and, if necessary, arbitrarily mixed with a filler, excipient, adjuvant or binder and further shaped into products in the form of a granule, sphere, short rod, plate, cubic or tablet before use.

The SACCHARIDES have a satisfactory sweetness that well harmonizes with tastable substances with sourness, saltiness, astringency, taste or bitterness, and have relatively strong acid- and heat-tolerances. Thus, the SACCHARIDES can be arbitrarily used to sweeten food products in general and to improve their taste and quality.

The SACCHARIDES can be favorably used as various types of seasonings such as soy sauce, soy sauce powder, miso, miso powder, "moromi" (unrefined soy sauce), "hishio" (miso sauce mixed with salted vegetables), "furikake" (fish or laver flour), mayonnaise, dressing, vinegar, "sanbai-zu" (sauce mixing sake, soy and vinegar). "funmatsu-sushi-su" (powdered vinegar for sushi), "chuka-no-moto" (Chinese taste seasoning), "tentsuyu" (soup for tenpura), "mentsuyu" (soup for Japanese-style noodles), sauce, ketchup, "takuan-zuke-no-moto" (seasoning for Japanese radish), "hakusai-zuke-no-moto" (seasoning for Chinese cabbage), "yakiniku-no-tare" (soup for grilled meat), curry roux, stew premix, soup premix, "dashi-no-moto" (dried bonito taste seasoning), mixed seasoning, "mirin" (heavily sweetened sake), "shin-mirin" (synthetic mirin), table sugar and coffee sugar.

In addition, the SACCHARIDES can be favorably used to sweeten, for example, Japanese-style confectioneries such as "senbei" (rice cracker), "arare" (glutinous rice cracker), "okoshi" (millet and rice cracker), rice cake, "manju" (bun with a bean-jam filling), "uiro" (sweet rice jelly), "an" (bean jam), "yokan" (sweet jelly of beans), "mizu-yokan" (soft adzuki-bean jelly), "kingyoku" (jelly-like Japanese cake), jelly, pao de Castella, and "amedama" (Japanese-style toffee); Western-style confectioneries such as bun, biscuit, cracker, cookie, pie, pudding, butter cream, custard cream, cream puff, waffle, sponge cake, doughnut, chocolate, chewing gum, caramel and candy; frozen desserts such as ice cream and sherbet; syrups such as those for fruit preserve and "kaki-gori" (shaved ice); pastes such as flour paste, peanut paste, fruit paste, and spread; processed fruits and vegetables such as jam, marmalade, syrup-preserved fruit and crystallized fruit; pickled products such as "fukujin-zuke" (sliced vegetables pickled in soy sauce), "bettara-zuke" (fresh radish pickles), "senmai-zuke" and "rakkyo-zuke" (pickled shallots); meat products such as ham and sausage; fish meat products such as fish meat ham, fish meat sausage, "kamaboko" (boiled fish paste), "chikuwa" (bamboo wheels shaped kamaboko) and "tenpura" (deep fried foods); relishes such as "uni-no-shiokara" (salted guts of sea urchin), "ika-no-shiokara" (salted guts of squid), "su-konbu", "saki-surume" and "fugu-no-mirinboshi"; "tsukudani" (food boiled down in soy sauce) such as those of "nori" (dried seaweed), "sansai" (mountain vegetables), "surume" (dried squid), small fish and shellfish; daily dishes such as "nimame" (cooked beans), potato salad and "konbu-maki" (tangle roll); milk products; bottled and canned products such as those of meat, fish meat, fruit and vegetable; alcoholic drinks such as synthetic sake, liqueur, wine and whisky; beverages such as coffee, tea, cocoa, juice, carbonated beverage, lactic acid beverage and lactobacillus beverage; premixes and instant foodstuffs such as pudding premix, hot cake premix, "sokuseki-shiruko" (premix of adzuki-bean soup with rice cake), and instant soup; and beverages such as baby foods, therapeutic foods, and nutrient beverages; and to improve their tastes and qualities.

Furthermore, the SACCHARIDES can be used in feeds and pet foods for domestic animals and poultry including honey bees, silkworms and fish so as to improve their taste preference. They can be also favorably used as a sweetener for products in the form of a solid, paste or liquid including cosmetics and pharmaceuticals such as a dentifrice, lipstick, lip cream, internal medicine, tablet, troche, cod-liver oil drop, oral refreshing agent, cachou and gargle, and also used as a taste quality-improving agent, taste-masking agent or quality-improving agent.

When used as a quality-improving agent or a stabilizer, the SACCHARIDES are favorably usable in biologically active substances susceptible to loss of their effective ingredients and activities, and in health foods and pharmaceuticals containing such biologically active substances. The SACCHARIDES facilitate the preparation of high-quality health foods and pharmaceuticals with a satisfactory stability without losing their effective ingredients and activities by incorporating into solutions containing vitamins such as thiamine, riboflavin, L-ascorbic acid, cod-liver oil, carotenoid, ergosterol and tocopherol; those containing enzymes such as lipase, elastase, urokinase, protease, β-amylase, isoamylase, glucanase and lactase; extracts such as ginseng extract, snapping turtle extract, chlorella extract, aloe extract, and propolis extract; living microorganisms such as virus, lactic acid bacteria, and yeast; or biologically active substances such as royal jelly.

To incorporate the SACCHARIDES into the aforesaid various compositions, conventional methods, for example, mixing, kneading, dissolving, melting, soaking, permeating, spreading, applying, coating, spraying, injecting and solidifying are appropriately chosen before completion of their preparations. The SACCHARIDES are usually incorporated into the desired compositions in an amount of at least 0.1%, desirably, at least 0.5%, d.s.b. The SACCHARIDES can be used as sweeteners with an anti-caries activity and arbitrarily mixed with sucrose into compositions in which the dental-caries inducibility of sucrose is well inhibited. When used with sucrose, the SACCHARIDES are incorporated into the compositions in an amount of at least 5%, preferably, at least 10% to sucrose, d.s.b. The methods to use the above compositions, i.e. the present growth-promoting agent for bifid bacteria and the present anti-caries agent, are adequately chosen depending on the types of compositions used, the content of α-isomaltosyl α-glucoside, α-isomaltosyl α-isomaltoside, and α-isomaltotriosyl α-glucoside as effective ingredients, and on the frequency of their administrations. Usually, one or more of the effective ingredients are suitably administered to human daily at a dose of about 0.1–100 g/day/adult, preferably, about 0.5–30 g/day/adult.

The administration of the present compositions, having activities to promote the growth of bifid bacteria and to prevent caries, to animals including human induces a predominant growth of bifid bacteria in their intestines, especially, in their large intestines to produce organic acids such as acetic acid and lactic acid and to lower their intestinal pH levels. The present compositions inhibit the growth of infectious—and putrefactive-bacteria and inhibit the formation of harmful substances which are inevitably formed during the metabolization of amino acids and proteins. Furthermore, the present compositions appropriately stimulate the intestines to adequately promote the peristalsis, increase the amount of feces, effectively control the intestinal conditions, and prevent constipation. The present compositions have an activity of promoting the mineral absorption, for example, of calcium, magnesium, iron, copper, zinc and phosphorous.

Thus, the present compositions with activities to promote the growth of bifid bacteria and to inhibit caries can be arbitrarily used by men and women of all ages to maintain and promote their beauty and health, prevent geratic diseases, recover and promote their health during or after diseases, and treat and/or prevent hyperammonemia, hepatic encephalopathy, and osteoporosis.

In addition, the present compositions exert their satisfactory effect on domestic animals such as pig, dog and cat, poultry such as canary, parakeet and chicken, and other animals such as honey bees, silk warms and fishes: For example, they can prevent these animals from infectious diseases, suppress their unfavorable smell of feces, promote the animals' growth and egg-laying, and promote the mineral absorption.

The SACCHARIDES are readily processed with sucrose into compositions which positively prevent the sucrose cariogenicity: When used with sucrose, the SACCHARIDES are added to sucrose in an amount of at least 5%, preferably at least 10% to sucrose, d.s.b. The following experiments explain the present invention in more detail:

Experiment 1
Preparation of α-isomaltosyl α-glucoside, α-isomaltosyl α-isomaltoside, and α-isomaltotriosyl α-glucoside Sixty parts by weight of trehalose and 40 parts by weight of maltotetraose, which are commercialized by Hayashibara Biochemical Laboratories, Inc., Okayama, Japan, were dissolved by heating in 150 parts by weight of water, and the solution was adjusted to 60° C. and pH 5.5, mixed with 5 units/g maltotetraose of "TRANSGLUCOSIDASE", an α-glucosidase specimen from a microorganism of the species Aspergillus niger, commercialized by Amano Pharmaceutical Co., Ltd., Aichi, Japan, followed by successively subjecting an enzymatic reaction for 24 hours and heating at 100° C. for 20 min to inactivate the remaining enzyme. The resultant solution contained, on a dry solid basis, about 22% α-isomaltosyl α-glucoside, about 4% α-isomaltosyl α-isomaltoside, about 6% α-isomaltotriosyl α-glucoside, reducing saccharides such as glucose, maltose and maltotriose, and intact trehalose and maltotriose. The solution was decolored with an activated charcoal, desalted and purified with ion exchangers of H- and OH-form, concentrated into an about 50 w/v % solution which was then subjected to column chromatography using a column packed with a strong-acid cation exchanger to collect fractions rich in α-isomaltosyl α-glucoside.

"XT-1016 ($Na^+$-form, polymerization degree of 4%)", a strong-acid alkali-metal cation exchanger commercialized by Tokyo Organic Chemical Industries, Ltd., Tokyo, Japan, was used as a resin for fractionation after suspended in water and packed in a jacketed stainless steel column having an inner column diameter of 5.4 cm. In this case, four columns, having a gel-bed depth of 5 m each, were cascaded in series to give a total gel-bed depth of about 20 m. While keeping the columns at 60° C., 5 v/v % of a saccharide solution as a material feed was fed to the columns, fractionated by feeding 60° C. hot water to the columns at an SV (space velocity) 1.5 to separately collect fractions rich in α-isomaltosyl α-glucoside and other fractions rich in α-isomaltosyl α-isomaltoside and α-isomaltotriosyl α-glucoside.

The fractions rich in α-isomaltosyl α-isomaltoside and α-isomaltotriosyl α-glucoside were pooled and prepared into an about 2 w/v % solution which was then adjusted to give a pH 5.0, mixed with 5 units/g dry solid of glucoamylase, and incubated at 40° C. for 20 hours to mainly decompose concomitant saccharides having α-1,4 glucosidic linkages at their non-reducing ends. Thereafter, the resultant mixture was heated at 100° C. for 20 min to inactivate the remaining enzyme, cooled, and in usual manner desalted, purified and concentrated into an about 40 w/v % solution which was then column chromatographed using a column packed with "YMC-PACK R-355-15", an octadecyl silica gel commercialized by YMC Co., Ltd., Kyoto, Japan, to separately collect fractions rich in α-isomaltosyl α-isomaltoside and other fractions rich in α-isomaltosyl α-glucoside. The α-isomaltosyl α-isomaltoside rich fractions were collected by repeating the above process, pooled, desalted, purified, concentrated, and dried in vacuo to obtain an about 2 parts by weight of a powdery α-isomaltosyl α-isomaltoside. The powdery product contained about 97% α-isomaltosyl α-isomaltoside, d.s.b.

Similarly as above, about 12 parts by weight of an α-isomaltosyl α-glucoside rich powder containing about 98% α-isomaltosyl α-glucoside, d.s.b., and about 3 parts by weight of an α-isomaltotriosyl α-glucoside rich powder containing about 97% α-isomaltotriosyl α-glucoside, d.s.b., were obtained.

Experiment 2
Physicochemical property of α-isomaltosyl α-isomaltoside

The physicochemical property of α-isomaltosyl α-isomaltoside was studied using a powdery product rich in α-isomaltosyl α-isomaltoside:

(1) Elemental analysis Found: C=42.1%, H=6.3%, O=51.6% Theoretical value: C=41.98%, H=6.17%, O=51.85% (Chemical formula: $C_{24}H_{42}O_{21}$);

(2) Molecular weight 666.6 Daltons;

(3) Ultraviolet ray absorption Exhibiting no characteristic absorption when measured after dissolving in water;

(4) Taste Exhibiting about ⅕ sweetening power of sucrose, and having a satisfactory taste and no unfavorable smell;

(5) Solubility in solvent Readily soluble in water, 0.1N NaOH and 0.1N HCl. Hardly soluble in methanol and ethanol. Insoluble in chloroform and ethyl acetate;

(6) Coloring reaction Exhibiting green on the anthrone-sulfonic acid reaction. Negative on the Fehling reaction and the iodine reaction;

(7) Structure
  (a) Only forming D-glucose residues when hydrolyzed with 1N sulfuric acid;
  (b) Analysis of methylhexytolacetate on gas chromatography revealed that 1,5-di-O-acetyl -2,3,4,6-tetra-O-methylglucitol and 1,5, 6-tri-O-acetyl-2, 3, 4-tri-O-methylglucitol are formed in a molar ratio of 1:1 after successive methylation, hydrolysis with an acid, reduction, and acetylation into glycitolacetate or methylhexytolacetate;
  (c) Being partially hydrolyzed by glucoamylase into glucose, trehalose and α-isomaltosyl α-glucoside but not hydrolyzed by isomaltodextranase; and
  (d) Twelve $^{13}C$ signals were observed on $^{13}C$-NMR (nuclear magnetic resonance) and assigned to the chemical shifts of α-D-glucopyranose as a standard substance as reported by J. H. Bradbury in "*Carbohydrate Research*", Vol.126, pp.125–156(1984), revealing that the powdery product was a saccharide composed of O-α-D-glucopyranosyl-(1→6)-α-D-glucopyranoside. The results of the molecular weight and the sugar component analysis show that the powdery product was a tetrasaccharide composed of glucose residues. The number of $^{13}C$ signals of the sample is half of that of 24 carbon atoms, indicating that it has a symmetric structure to a point, i.e. a structure of O-α-D-glucopyranosyl-(1→6)-α-D-glucopyranosyl O-α-D-glucopyranosyl-(1→6)-α-D-glucopyranoside.

Based on these results, the structure of the powdery product can be shown as in FIG. 1.

The structure named the powdery product α-isomaltosyl α-isomaltoside.

Figure 2:
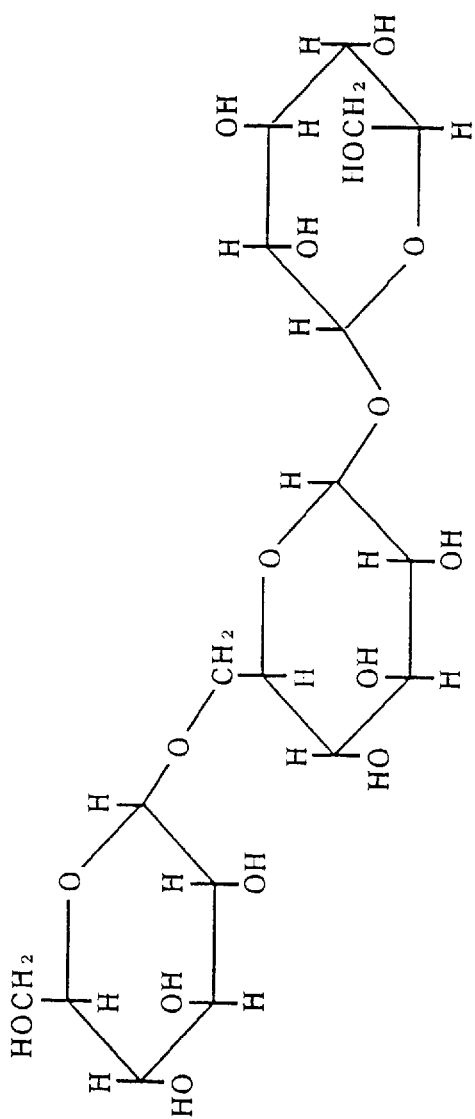
FIG. 2 is a figure of the structure of α-isomaltosyl α-glucoside.
Figure 3:
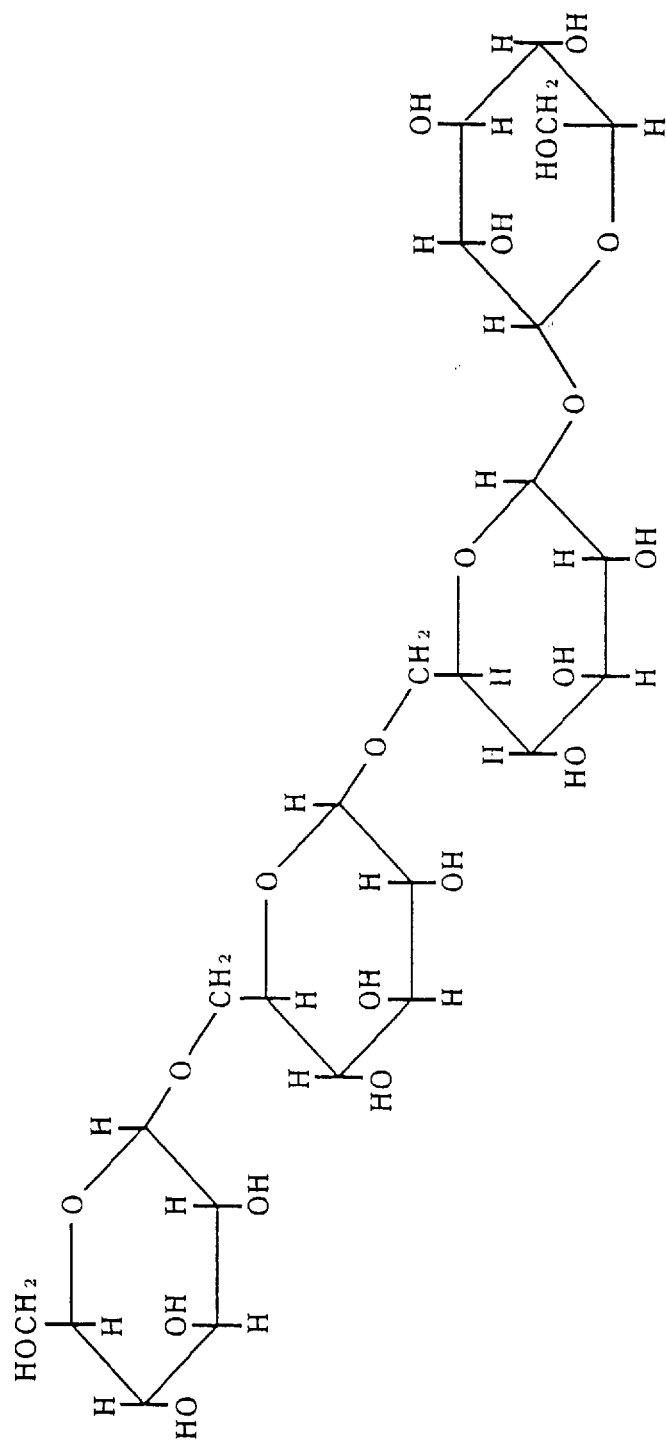
FIG. 3 is a figure of the structure of α-isomaltotriosyl α-glucoside.

The physicochemical properties and analytic results of α-isomaltosyl α-glucoside and α-isomaltotriosyl α-glucoside, which were obtained similarly as α-isomaltosyl α-isomaltoside, reveal that these substances are respectively O-α-D-glucopyranosyl -(1→6)-α-D-glucopyranosyl α-D-glucopyranoside and O-α-D-glucopyranosyl-(1→6)-O-α-D-glucopyranosyl-(1→6) α-D-glucopyranosyl α-D-glucopyranoside having structures as in FIGS. 2 and 3.

Experiment 3
Maillard reaction

A solution, consisting of 10 w/v % α-isomaltosyl α-glucoside prepared by the method in Experiment 1, one w/v % glycine, and 50 mM phosphate buffer (pH 7.0), was incubated at 100° C. for 90 min, cooled, and measured for absorbency at a wavelength of 480 nm in a 1-cm light-path cell. Similarly, α-isomaltosyl α-isomaltoside and α-isomaltotriosyl α-glucoside were tested. As a control, trehalose, isomaltose, isomaltotriose and isomaltotetraose were tested similarly as above. The results were in Table 1:

TABLE 1

| Saccharide | Coloration degree (at a wavelength of 480 nm) |
|---|---|
| Trehalose | 0.007 |
| Isomaltose | 0.938 |
| Isomaltotriose | 0.642 |
| Isomaltotetraose | 0.495 |
| α-Isomaltosyl α-glucoside | 0.021 |
| α-Isomaltosyl α-isomaltoside | 0.016 |
| α-Isomaltotriosyl α-glucoside | 0.019 |

As is evident from the results in Table 1, it was revealed that α-isomaltosyl α-glucoside as the present effective ingredient gave a relatively-low coloration degree which equals to about 3% of that of isomaltotriose as a reducing saccharide having the same degree of glucose polymerization (DP) as α-isomaltosyl α-glucoside, and, similarly as trehalose, the effective ingredient is a saccharide substantially free from the Maillard reaction. It was also found that α-isomaltosyl α-isomaltoside and α-isomaltotriosyl α-glucoside are saccharides substantially free from the Maillard reaction similarly as α-isomaltosyl α-glucoside.

Experiment 4
Digestion test

In accordance with the method as reported by Okada et al. in "*Journal of Japanese Society of Nutrition and Food Science*", Vol.43, No.1, pp.23–29(1990), α-isomaltosyl α-glucoside prepared by the method in Experiment 1 was tested for digestibility in vitro, and the digestion level was evaluated based on the hydrolysis rate (the ratio of glucose to the total sugars). α-Isomaltosyl α-isomaltoside and α-isomaltotriosyl α-glucoside, prepared by the method in Experiment 1, were tested similarly as above. As a control, maltose, trehalose and isomaltose were tested similarly as above. The results were in Table 2:

TABLE 2

| | Decomposition rate (%) = (glucose/total sugars) × 100 | | | |
|---|---|---|---|---|
| Saccharide | Salivary amylase | Gastric acid | Pancreatic juice amylase | Enzyme from small intestinal mucus membrane |
| Maltose | 0.0 | 0.0 | 0.2 | 80.1 |
| Trehalose | 0.0 | 0.0 | 0.0 | 1.3 |
| Isomaltose | 0.0 | 0.0 | 0.2 | 13.2 |
| α-Isomaltosyl α-glucoside | 0.0 | 0.0 | 0.5 | 5.3 |
| α-Isomaltosyl α-isomaltoside | 0.0 | 0.0 | 0.3 | 6.0 |
| α-Isomaltotriosyl α-glucoside | 0.0 | 0.0 | 0.5 | 8.8 |

As is evident from the results in Table 2, it can be conceived that most of the present α-isomaltosyl α-glucoside reaches up to the large intestines when orally administered because it is slightly hydrolyzed predominantly by the enzymes of small intestinal mucus membranes, while maltose and isomaltose are decomposed predominantly by the enzymes. Although α-isomaltosyl α-isomaltoside and α-isomaltotriosyl α-glucoside are slightly different from α-isomaltosyl α-glucoside on their decomposition rate by the enzymes, they can be judged to be relatively-low in digestibility or relatively-low in calorie similarly as α-isomaltosyl α-glucoside.

Experiment 5
Assimilation test by intestinal microorganism

Intestinal microorganisms were cultured at 37° C. for 96 hours in PYF broth (peptone yeast extract fildes solution broth) as reported by Tomotari MITSUOKA in "*A Color Atlas of Anaerobic Bacteria*", published by Kabushiki Kaisha Sobunsha, Tokyo, Japan, page 325(1984), which had been supplemented with or without 0.5 w/v % of α-isomaltosyl α-glucoside prepared by the method in Experiment 1. To evaluate the growth rate of and to judge the assimilability by the microorganisms, the resultant broth was diluted 5-fold, and the turbidity of the dilution was measured at a wavelength of 750 nm in a 1-cm light-path cell. The α-isomaltosyl α-isomaltoside and α-isomaltotriosyl α-glucoside prepared in Experiment 1 were tested similarly as above. As a control, glucose, trehalose and isomaltose were tested similarly as above. The criteria were in Table 3, and the results were in Tables 4 and 5:

TABLE 3

| Turbidity at a wavelength of 750 nm (×5) | Judgement |
| --- | --- |
| Less than 0.1 | − |
| 0.1 or higher but less than 0.15 | ± |
| 0.15 or higher but less than 0.2 | + |
| 0.2 or higher but less than 0.3 | ++ |
| 0.3 or higher | +++ |

TABLE 4

| Strain of microorganism | Free of sugar | Saccharide | | | | | |
| --- | --- | --- | --- | --- | --- | --- | --- |
| | | A | B | C | D | E | F |
| *Bifidobacterium adolescentis* JCM 1275 | − | +++ | + | +++ | +++ | +++ | +++ |
| *Bifidobacterium animalis* JCM 1190 | − | +++ | + | +++ | +++ | +++ | +++ |
| *Bifidobacterium bifidum* JCM 1255 | − | ++ | + | + | ++ | ++ | ++ |
| *Bifidobacterium breve* JCM 1192 | − | ++ | − | +++ | +++ | +++ | +++ |
| *Bifidobacterium infantis* JCM 1222 | − | ++ | − | +++ | +++ | +++ | ++ |
| *Bifidobacterium longum* JCM 1217 | − | +++ | ++ | ++ | +++ | +++ | |
| *Lactobacillus fermentum* IFO 3959 | − | ++ | + | − | − | − | − |
| *Lactobacillus plantarum* IFO 3070 | − | ++ | ++ | − | − | − | − |
| *Eubacterium aerofaciens* ATCC 25986 | − | +++ | − | + | − | − | − |
| *Bacteroides distasonis* JCM 5825 | − | ++ | ++ | + | − | − | − |

Note:
In the Table, the symbols "A" to "F" mean:
A, glucose;
B, trehalose;
C, isomaltose;
D, α-isomaltosyl α-glucoside;
E, α-isomaltosyl α-isomaltoside;
and F, α-isomaltotriosyl α-glucoside.

TABLE 5

| Strain of microorganism | Free of sugar | Saccharide | | | | | |
| --- | --- | --- | --- | --- | --- | --- | --- |
| | | A | B | C | D | E | F |
| *Bacteroides vulgatus* JCM 5826 | − | + | + | − | − | − | − |
| *Bacteroides uniformis* JCM 5828 | − | ++ | ++ | − | − | − | − |
| *Clostridium butyricum* JCM 1391 | − | +++ | +++ | ++ | ++ | +++ | +++ |
| *Clostridium perfringens* JCM 3816 | − | +++ | +++ | ± | + | − | ± |
| *Clostridium ramosum* JCM 1298 | − | + | + | − | − | − | − |
| *Clostridium sporogenes* JCM 1416 | ± | + | ++ | ± | ± | ± | ± |
| *Streptococcus faecalis* IAM 10065 | − | ++ | + | + | − | − | − |
| *Peptostreptococcus prevotii* ATCC 9321 | − | + | + | − | ± | ± | ± |
| *Escherichia coli* IFO 3301 | − | + | − | − | − | − | − |

Note:
In the Table, the symbols "A" to "F" mean:
A, glucose;
B, trehalose;
C, isomaltose;
D, α-isomaltosyl α-glucoside;
E, α-isomaltosyl α-isomaltoside;
and F, α-isomaltotriosyl α-glucoside.

As is evident from the results in Tables 4 and 5, it was revealed that, unlike glucose and trehalose as a control, the present α-isomaltosyl α-glucoside, α-isomaltosyl α-isomaltoside and α-isomaltotriosyl α-glucoside are high in the selective assimilability by bifid bacteria. Considering these results and those in Experiment 4 in combination, it can be judged that most of α-isomaltosyl α-glucoside, α-isomaltosy α-isomaltoside and α-isomaltotriosyl α-glucoside reach up to the large intestines and act as a growth-promoting agent for bifid bacteria when orally administered to mammals.

plying the quotient by 100. The relative change of the total number of bifid bacterial was calculated by multiplying the cell count of bifid bacteria per g of feces by the total feces' weight, and the total cell count of bifid bacteria after the 14-day administration test was expressed by a relative value when regarded the total cell count of bifid bacteria before the administration test as 100. The changes of the weight, the pH, and the total cell count of bifid bacteria in the volunteers' feces were summarized in Table 6:

TABLE 6

|  | α-Isomaltosyl α-isomaltoside | | α-Isomaltosyl α-glucoside | |
| --- | --- | --- | --- | --- |
|  | Before | After | Before | After |
| Weight of feces (g/day)* | 128± 32 | 142± 40 | 125± 33 | 140± 37 |
| Relative changes of* feces' weight | 100 | 111 | 100 | 112 |
| pH of feces* | 6.7± 0.5 | 5.9± 0.3 | 6.6± 0.5 | 6.0± 0.4 |
| Total microorganisms per g of feces** | 10.8± 0.2 | 10.9± 0.2 | 10.9± 0.2'1 | 10.9± 0.2 |
| Percentage (%) of bifid bacteria per g of feces** | 9.9± 0.2 | 10.3± 0.1 | 9.9± 0.2 | 10.3± 0.2 |
| Percentage (%) of bifid bacteria to the total microorganisms* | 12.3 | 25.0 | 12.3 | 24.5 |
| Relative changes of bifid bacteria* | 100 | 256 | 100 | 231 |

Note:
In the Table, the symbols "*" and "**" show a mean value or a mean value ± SD (standard deviation) and a relative mean value ± SD per g of feces, respectively.

Experiment 6

Influence on growth-promoting activity for bifid bacteria in vivo

Either 10 g α-isomaltosyl α-glucoside or 10 g α-isomaltosyl α-isomaltoside was dissolved in a hot soup and administered orally to five healthy volunteers, an average age of 40.6 and an average weight of 62.2 kg, at lunchtime daily for 14 days. This experiment procedure was as follows: Provide a control period for 14 days between a first administration test of α-isomaltosyl α-isomaltoside and a second administration test of α-isomaltosyl α-glucoside. The weight of daily feces before and after the 14-day administration tests, the relative change of feces' weight, the feces' pH, the total number of microorganisms per g of feces, the percentage of the number of bifid bacteria to the total number of microorganisms in feces, and the relative change of the total number of bifid bacteria were measured, followed by calculating the mean value of the five volunteers. Among these measurements, the total number of microorganisms was determined in accordance with the method as reported in "A Color Atlas of Anaerobic Bacteria", pp.53–65 (1984), edited by Tomotari MITSUOKA, published by Kabushiki Kaisha Sobunsha, Tokyo, Japan (1984): The colonies grown in 13 different types of media excluding M10 medium were judged for which genus they belong to and counted for cells. The cell count obtained with a specific medium, which gave the highest number of microorganisms for each genus, was determined to be a real cell count. The total cell count of microorganisms of all the genera was determined to be the total number of microorganisms in each volunteer's feces. The percentage (%) of bifid bacteria to the total microorganisms was calculated by dividing the cell count of bifid bacteria (microorganisms of the genus Bifidobacterium) by the total cell count of the total microorganisms and multi- As is evident from the results in Table 6, it was revealed that as compared with the data before the administration of α-isomaltosyl α-glucoside or α-isomaltosyl α-isomaltoside, the administration lowered the feces' pH by about 0.6–0.8 and increased the daily feces' amount, the cell count of bifid bacteria per g of feces, the percentage (%) of bifid bacteria to the total microorganisms in feces by about 2-fold where the total cell count of bifid bacteria increased by about 2.3- to 2.5-fold. Similarly as α-isomaltosyl α-glucoside and α-isomaltosyl α-isomaltoside, it was found that α-isomaltotriosyl α-glucoside is not readily digested in the gastric tracts and mostly reaches up to the large intestines to exert an effect to promote the growth of bifid bacteria when orally administered to human.

Experiment 7

Acid formation by dental caries-inducing microorganisms

By using α-isomaltosyl α-glucoside prepared by the method in Experiment 1 and according to the method reported by Kanou TAKEUCHI in "Japanese Journal of Oral Biology", Vol.26, pp.698–713(1984), it was studied whether the saccharide is fermented by Streptococcus sobrinus ATCC 27351 as a dental caries-inducing microorganism.

The experiment was as follows: Mix a 50 w/v % suspension of living wet cells in the Stephen buffer (pH 7.0) and a 0.02M solution of a test saccharide in the same buffer, stir the mixture at 37° C., and measure the pH at a prescribed time interval. Similarly as above, α-isomaltosyl α-isomaltoside and α-isomaltotriosyl α-glucoside were tested. As a control, sucrose, trehalose and isomaltose were tested similarly as above. The results were in Table 7:

TABLE 7

| Saccharide | pH at each fermentation time (min) | | | | | |
| --- | --- | --- | --- | --- | --- | --- |
| | 0 | 5 | 15 | 30 | 60 | 90 |
| Sucrose | 7.0 | 4.3 | 4.1 | 4.0 | 4.0 | 4.0 |
| Trehalose | 7.0 | 6.7 | 5.3 | 4.7 | 4.3 | 4.2 |
| Isomaltose | 7.0 | 7.0 | 6.9 | 6.9 | 6.8 | 6.7 |
| α-Isomaltosyl α-glucoside | 7.0 | 7.0 | 6.9 | 6.9 | 6.9 | 6.9 |
| α-Isomaltosyl α-isomaltoside | 7.0 | 7.0 | 6.9 | 6.9 | 6.9 | 6.9 |
| α-Isomaltotriosyl α-glucoside | 7.0 | 7.0 | 6.9 | 6.9 | 6.9 | 6.9 |

As is evident from the results in Table 7, it was revealed that rapid-, moderate- and slight-pH reductions were found in each case of using sucrose, trehalose and isomaltose. While in the case of using α-isomaltosy α-glucoside, no substantial pH reduction was found, meaning that the saccharide is substantially free of acid fermentation. It was also found that α-isomaltosyl α-isomaltoside and α-isomaltotriosyl α-glucoside are substantially free of acid fermentation similarly as α-isomaltosyl α-glucoside.

Experiment 8

Inhibition of insoluble glucan formation by glucosyltransferase from dental caries-inducing microorganism By using α-isomaltosyl α-glucoside prepared by the method in Experiment 1 and according to the method reported by Kanou TAKEUCHI in "Japanese Journal of Oral Biology", Vol.26, pp.698–713(1984), the effect of transglucosidase, derived from Streptococcus sobrinus strain (ATCC 27351), on the enzymatic synthesis of insoluble glucans from sucrose was studied.

To a mixture solution consisting of one ml of one w/v % sucrose solution, one ml of one w/v % of a test saccharide solution, and 1.5 ml of 0.1M phosphate buffer (pH 6.8) was added 0.5 ml solution containing a crude glucosyltransferase specimen in a total protein content of 10 mg, and the mixture solution was placed in a small test tube which was then fixed and slanted to give a grade 30 degrees and allowed to react at 37° C. for 16 hours. The reaction mixture was transferred gently to another test tube and mixed with a solution obtained by washing carefully with 4 ml water the remaining substances adhered to the inner walls of the small test tube, and the mixture solution was centrifuged to obtain a precipitate as a non-adsorbed glucan. The amounts of the adsorbed- and non-adsorbed glucans thus obtained were respectively quantified by the anthrone-sulfuric acid method, and the total amount of them was regarded as the amount of the formed insoluble glucans. As a control system, a reaction system using water in place of the test saccharide solution, i.e. a reaction system using sucrose as a saccharide, was provided. The inhibitory percentage of the formation of insoluble glucans was determined by subtracting from 100 the percentage (%) of the amount of the formed insoluble glucans, which had been formed in the test saccharide solution system, to that of the control system. α-Isomaltosyl α-isomaltoside and α-isomaltotriosyl α-glucoside prepared by the method in Experiment 1 were tested similarly as above. As a control, trehalose and isomaltose were tested similarly as above. The results were in Table 8:

TABLE 8

| Saccharide | Yield of non-adsorbed glucans (pg/ml) | Yield of adsorbed glucans (pg/ml) | Inhibitory percentage (%) on insoluble glucans formation |
| --- | --- | --- | --- |
| Sucrose alone (Control) | 923 | 1,160 | — |
| Sucrose plus trehalose | 1,130 | 772 | 8.7 |
| Sucrose plus isomaltose | 305 | 67 | 82.2 |
| Sucrose plus α-isomaltosyl α-glucoside | 118 | 30 | 92.9 |
| Sucrose plus α-isomaltosyl α-isomaltoside | 298 | 72 | 82.2 |
| Sucrose plus α-isomaltotriosyl α-glucoside | 269 | 66 | 83.9 |

As is evident from the results in Table 8, it was found that, as compared with sucrose as a control, α-isomaltosyl α-glucoside formed non-adsorbed- and adsorbed-glucans in an extremely small amount, and found that it more strongly inhibited the formation of insoluble glucans than trehalose and isomaltose as a control. It was also found that α-isomaltosyl α-isomaltoside and α-isomaltotriosyl α-glucoside, which were tested in parallel with α-isomaltosyl α-glucoside, strongly inhibited the formation of insoluble glucans similarly as α-isomaltosyl α-glucoside.

Considering totally these results and those in Experiment 7, α-isomaltosyl α-glucoside, α-isomaltosyl α-isomaltoside and α-isomaltotriosyl α-glucoside are not substantially fermented by dental caries-inducing microorganisms, inhibit the formation of insoluble glucans by such microorganisms, and effectively inhibit the adsorption of insoluble glucans on the plain surfaces of teeth. Therefore, it can be conceived that these saccharides positively inhibit the dental caries-inducibility of sucrose when used with sucrose, and this concludes that they are suitably used as a dental caries-inhibitory agent.

Experiment 9

Acute toxicity test

By using mice the α-isomaltosyl α-glucoside specimen in Experiment 1 was administered orally to the mice for acute toxicity test. As a result, no mouse died even when administered with a highest possible dose. This means that the $LD_{50}$ is 50 g/kg mouse or more and concludes that it is extremely low in toxicity. Similarly as above, the α-isomaltosyl α-isomaltoside and α-isomaltotriosyl α-glucoside specimens prepared in Experiment 1 were tested and revealing that their $LD_{50}$ are 50 g/kg mouse or more and these saccharides are extremely low in toxicity.

Examples A and B illustrate the process for preparing the present growth-promoting agent for bifid bacteria containing as an effective ingredient α-isomaltosyl α-glucoside or α-isomaltosyl α-isomaltoside and/or α-isomaltosyl α-glucoside, and the present composition with an activity to promote the growth of bifid bacteria, which contains as an effective ingredient α-isomaltosyl α-glucoside or α-isomaltosyl α-isomaltoside and/or α-isomaltosyl α-glucoside:

EXAMPLE A-1

One part by weight of trehalose and one part by weight of "PINE-DEX #4", a dextrin with a DE (dextrose equivalent) 18 commercialized by Matsutani Chemical Ind., Co., Ltd., Hyogo, Japan, were dissolved by heating in 2.5 parts by weight of water, and the solution was adjusted to 60° C. and pH 5.5, and mixed with 5 units/g dry solid of an α-glucosidase specimen from *Aspergillus niger* before a 20-hour enzymatic reaction, followed by incubating the reaction mixture at 95° C. for 30 min to inactivate the remaining enzyme. The resultant solution was in usual manner decolored with an activate charcoal, filtered, desalted and purified with ion exchangers of H- and OH-form, and concentrated to obtain a 75% syrup of α-isomaltosyl α-isomaltoside in a yield of about 92%, d.s.b.

The product, containing about 21% α-isomaltosyl α-glucoside, about 5% α-isomaltosyl α-isomaltoside, and about 7% α-isomaltotriosyl α-glucoside, d.s.b., can be suitably used as a growth-promoting agent for bifid bacteria, a mineral absorption-promoting agent, and an anti-caries agent. The product has a mild sweetness, moderate viscosity, and moisture-retaining ability, and because of these it can be arbitrarily used as a sweetener, taste-improving agent, stabilizer, filler, adjuvant and excipient in compositions such as food products, cosmetics and pharmaceuticals which have activities to promote the growth of bifid bacteria and the mineral absorption, and to prevent caries.

EXAMPLE A-2

A reaction mixture, obtained by the method in Example A-1, was purified and concentrated into a material saccharide solution with a concentration of 50 w/v %. To increase the α-glucoside content, the saccharide solution was, in accordance with the method in Experiment 1, subjected to ion-exchange column chromatography using "XT-1016", a strong-acid cation exchanger of Na-form, packed in 4 jacketed stainless steel columns, having an inner diameter of 5.4 cm, cascaded in series to give a total gel-bed depth of 20 m.

Five v/v % of a saccharide solution was added to the resin while keeping the inner column temperature at 60° C., followed by feeding to the columns 60° C. hot water at an SV (space velocity) 0.15 to obtain fractions rich in α-isomaltosyl α-glycoside while removing concomitant saccharides such as maltose and glucose. The fractions were pooled, purified, concentrated, dried in vacuo, and pulverized to obtain a powder rich in α-isomaltosyl α-isomaltoside in a yield of about 25%, d.s.b.

The product, containing about 20% α-isomaltosyl α-isomaltoside, about 32% α-isomaltosyl α-glucoside, and about 28% α-isomaltotriosyl α-glucoside, d.s.b., can be suitably used as a growth-promoting agent for bifid bacteria, mineral absorption-promoting agent, and anti-caries agent. Since the product has a relatively low reducibility and a mild and high quality sweetness, it can be arbitrarily used as a sweetener, taste-improving agent, stabilizer, filler, excipient and adjuvant in compositions such as food products, cosmetics and pharmaceuticals which have activities to promote the growth of bifid bacteria and the mineral absorption, and to prevent caries.

EXAMPLE A-3

To 10 w/v % potato starch suspension was added calcium carbonate to give a final concentration of 0.1 w/v %, and the resultant suspension was adjusted to pH 6.0, mixed with 0.1% per g starch of "SPITASE HS", an α-amylase specimen commercialized by Nagase Biochemicals, Ltd., Kyoto, Japan, gelatinized and liquefied under stirring and heating conditions. The mixture was promptly autoclaved at 120° C. for 20 min and adjusted to 40° C. and pH 6.5. To the resultant mixture was added 500 units/g starch, d.s.b., of an isoamylase specimen commercialized by Hayashibara Biochemical-Laboratories, Inc., Okayama, Japan, 3 units/g starch, d.s.b., of a non-reducing saccharide-forming enzyme derived from Arthrobacter sp. Q36 (FERM BP-4316) as disclosed in Japanese Patent Application No.79,29194 applied by the present applicant, and 15 units/g starch, d.s.b., of a trehalose-releasing enzyme derived from the same strain, followed by an enzymatic reaction for 12 hours to obtain a saccharide solution containing about 55% trehalose, d.s.b. Thereafter, the saccharide solution was incubated at 95° C. for 30 min to inactivate the remaining enzyme, concentrated up to give a concentration of 45 w/v %, d.s.b., and adjusted to 60° C. and pH 5.0, then mixed with 3 units/g dry solid of an α-glucosidase specimen derived from *Candida tropicalis* strain (IFO 0589) commercialized by Hayashibara Biochemical Laboratories, Inc., Okayama, Japan, and subjected to an enzymatic reaction for 24 hours. The reaction mixture was incubated at 95° C. for 30 min to inactivate the remaining enzyme and in usual manner decolored with an activated charcoal, filtered, desalted and purified with ion exchangers of H- and OH-form, and concentrated into an about 75% syrup of α-isomaltosyl α-glucoside in a yield of about 95%, d.s.b.

The product, containing about 20% α-isomaltosyl α-glucoside, about 3% α-isomaltosyl α-isomaltoside, and about 5% α-isomaltotriosyl α-glucoside, d.s.b., can be suitably used as a growth-promoting agent for bifid bacteria, mineral absorption-promoting agent, and anti-caries agent. Since the product has a relatively low reducibility and a mild and high quality sweetness, it can be arbitrarily used as a sweetener, taste-improving agent, stabilizer, filler, excipient and adjuvant in compositions such as food products, cosmetics and pharmaceuticals which have activities to promote the growth of bifid bacteria and the mineral absorption, and to prevent caries.

EXAMPLE A-4

To 30 w/v % corn starch suspension was added calcium carbonate to give a final concentration of 0.1 w/v %, and the suspension was adjusted to pH 6.5, mixed with 0.2 w/v % per g starch of "TERMAMYL 60L", an α-amylase specimen commercialized by Novo Industri A/S, Copenhagen, Denmark, and heated while stirring to gelatinize and liquefy the starch. The resultant mixture was promptly autoclaved at 120° C. for 20 min, cooled to 55° C., mixed with 500 units/g starch, d.s.b., of an isoamylase specimen commercialized by Hayashibara Biochemical Laboratories, Inc., Okayama, Japan, and 30 units/g starch, d.s.b., of a β-amylase specimen commercialized by Nagase Biochemicals, Ltd., Kyoto, Japan, and subjected to an enzymatic reaction for 48 hours to obtain a saccharide solution containing about 84% maltose, d.s.b. The saccharide solution was heated at 95° C.

for 30 min and adjusted to 60° C. and pH 7.0, then mixed with one unit/g starch, d.s.b., of a maltosetrehalose converting enzyme derived from Thermus aquaticus strain (ATCC 33923) as disclosed in Japanese Patent Application No.144, 09294 applied by the present applicant, and subjected to an enzymatic reaction for 24 hours to obtain a saccharide solution containing about 50% trehalose, d.s.b. The saccharide solution thus obtained was adjusted to pH 5.5, mixed with 3 units/g dry solid of an α-glucosidase specimen derived from a microorganism of the species *Aspergillus niger*, and subjected to an enzymatic reaction at 60° C. for 24 hours. Thereafter, the resultant mixture was incubated at 95° C. for 30 min to inactivate the remaining enzyme and in usual manner successively decolored with an activated charcoal, filtered, desalted and purified with ion exchangers of H- and OH-form, concentrated, dried in vacuo, and pulverized to obtain a powder containing α-isomaltosyl α-glucoside in a yield of about 90%, d.s.b.

The product, containing about 20% α-isomaltosyl α-glucoside, about 4% α-isomaltosyl α-isomaltoside, and about 6% α-isomaltotriosyl α-glucoside, d.s.b., can be suitably used as a growth-promoting agent for bifid bacteria, mineral absorption-promoting agent, and anti-caries agent. Since the product has a mild sweetness, moderate viscosity, and moisture retaining ability, it can be arbitrarily used as a sweetener, taste-improving agent, stabilizer, filler, compositions such as food compositions such as food products, cosmetics and pharmaceuticals which have activities to promote the growth of bifid bacteria and the mineral absorption, and to prevent caries.

EXAMPLE A-5

To 30 w/v % of a potato starch suspension was added calcium carbonate to give a final concentration of 0.1 w/v %, and the suspension was adjusted to pH 6.5, mixed with 0.01% per g starch, d.s.b., of "SPITASE HS", an α-amylase specimen commercialized by Nagase Biochemicals, Ltd., Kyoto, Japan, and heated under stirring conditions to gelatinize and liquefy the starch. The mixture was promptly autoclaved at 120° C. for 5 min and cooled to 55° C. to obtain a liquefied starch solution with a DE (dextrose equivalent) of less than one, adjusted to pH 7.0, mixed with 150 units/g starch, d.s.b., of a pullulanase specimen and 8 units/g starch, d.s.b., of a malotetraose-forming amylase, both of which are commercialized by Hayashibara Biochemical Laboratories, Inc., Okayama, Japan, and subjected to an enzymatic reaction at 50° C. for 36 hours. The reaction mixture was successively incubated at 95° C. for 30 min, cooled to 45° C., mixed with 2 units/g starch, d.s.b., of a non-reducing saccharide forming enzyme derived from Rhizobium sp. M-11 (FERM BP-4130) as disclosed in European Patent Publication No.0606753 A2 applied by the present applicant before an enzymatic reaction for 64 hours, adjusted to 60° C. and pH 5.0, mixed with 3 units/g starch, d.s.b., of an α-glucosidase specimen from *Candida tropicalis* strain (IFO 0589), and subjected to an enzymatic reaction for 24 hours. The reaction mixture was incubated at 95° C. for 30 min to inactivate the remaining enzyme and in usual manner successively decolored with an activated charcoal, filtered, desalted and purified with ion exchangers of H- and OH-form, concentrated, dried in vacuo, and pulverized to obtain a powder containing α-isomaltosyl α-glucoside in a yield of about 90%, d.s.b.

The product, containing about 18% α-isomaltosyl α-glucoside, about 4% α-isomaltosyl α-isomaltoside, and about 5% α-isomaltotriosyl α-glucoside, d.s.b., can be suitably used as a growth-promoting agent for bifid bacteria, mineral absorption-promoting agent, and anti-caries agent. Since the product has a mild sweetness, appropriate viscosity, and satisfactory moisture-retaining ability, it can be arbitrarily used as a sweetener, taste-improving agent, stabilizer, filler, excipient and adjuvant in compositions such as food products, cosmetics and pharmaceuticals which have activities to promote the growth of bifid bacteria and the mineral absorption, and to prevent caries.

EXAMPLE A-6

To 30 w/v % of corn starch suspension was added calcium carbonate to give a final concentration of 0.1 w/v %, and the suspension was adjusted to pH 6.5, mixed with 0.3 w/v %. "TERMAMYL 60L", an α-amylase specimen commercialized by Novo Industri A/S Copenhagen, Denmark, and heated under stirring conditions to gelatinize and liquefy the starch. The mixture was promptly autoclaved at 120° C. for 30 min and cooled to 55° C. to obtain a liquefied starch solution with a DE of about 4, and the liquefied solution was mixed with 4 units/g starch, d.s.b., of a non-reducing saccharide-forming enzyme derived from Arthrobacter sp. Q36 (FERM BP-4316), 300 units/g starch, d.s.b., of an isoamylase specimen, and 5 units/g starch, d.s.b., of a cyclomaltodextrin glucanotransferase specimen, both of which are commercialized by Hayashibara Biochemical Laboratories, Inc., Okayama, Japan, and enzymatically reacted at pH 6.3 and 45° C. for 48 hours. The reaction mixture was incubated at 95° C. for 30 min to inactivate the remaining enzyme, adjusted to 55° C. and pH 5.5, and subjected an enzymatic reaction for 16 hours after mixed with 10 units/g starch, d.s.b., of β-amylase. Thereafter, the reaction mixture was incubated at 95° C. for 30 min to inactivate the remaining enzyme, cooled to 60° C., mixed with 3 units/g dry solid of an α-glucosidase specimen derived from a microorganism of the species *Aspergillus niger*, and subjected to an enzymatic reaction for 24 hours. The reaction mixture was kept at 95° C. for 30 min to inactivate the remaining enzyme and in usual manner successively decolored with an activated charcoal, filtered, desalted and purified with ion exchangers of H- and OH-form, and concentrated to obtain a syrup containing α-isomaltosyl α-glucoside in a yield of about 95%, d.s.b.

The product, containing about 18% α-isomaltosyl α-glucoside, about 2% α-isomaltosyl α-isomaltoside, and about 3% α-isomaltotriosyl α-glucoside, d.s.b., can be suitably used as a growth-promoting agent for bifid bacteria, mineral absorption-promoting agent, and anti-caries agent. Since the product has a mild sweetness, appropriate viscosity, and satisfactory moisture-retaining ability, it can be arbitrarily used as a sweetener, taste-improving agent, stabilizer, filler, excipient and adjuvant in compositions such as food products, cosmetics and pharmaceuticals which have activities to promote the growth of bifid bacteria and the mineral absorption, and to prevent caries.

EXAMPLE A-7

A reaction mixture obtained by the method in Example A-1 was in usual manner purified and concentrated into a 50 w/v % syrup which was then placed in an autoclave, admixed with 10 w/v % Raney nickel, heated up to a temperature of 90°–120° C. under gentle stirring conditions, and hydrogenated completely while increasing the hydrogen pressure up to 20–120 kg/cm². Thereafter, the Raney nickel was removed from the reaction mixture, and the resultant solution was decolored, desalted, purified and concentrated to obtain a 70 w/v % syrup in a yield of 80%, d.s.b. The product, containing about 21% α-isomaltosyl α-glucoside, about 5% α-isomaltosyl α-isomaltoside, about 7% α-isomaltotriosyl α-glucoside, d.s.b., and sugar alcohols, can be suitably used as a growth-promoting agent for bifid bacteria, mineral absorption-promoting agent, and anti-caries agent. The product has no reducibility but has a mild sweetness, appropriate viscosity, satisfactory moisture-retaining ability, and because of these it can be arbitrarily used as a sweetener, taste-improving agent, stabilizer, filler, excipient, adjuvant in compositions such as food products, cosmetics and pharmaceuticals which have activities to promote the growth of bifid bacteria and the mineral absorption, and to prevent caries.

EXAMPLE A-8

A fraction rich in α-isomaltosyl α-isomaltoside, obtained by the method in Example A-2, was in usual manner purified and concentrated into an about 50 w/v % syrup which was then, in accordance with the method in Example A-7, hydrogenated, purified, concentrated in vacuo, and pulverized to obtain a powder rich in α-isomaltosyl α-isomaltoside in a yield of about 70%, d.s.b. The product, containing about 32% α-isomaltosyl α-glucoside, about 20% α-isomaltosyl α-isomaltoside, about 28% α-isomaltotriosyl α-glucoside, d.s.b., and sugar alcohols, can be suitably used as a growth-promoting agent for bifid bacteria, mineral absorption-promoting agent, and anti-caries agent. The product has no reducibility but has a mild and high quality sweetness, and because of these it can be arbitrarily used as a sweetener, taste-improving agent, quality-improving agent, stabilizer, filler, excipient, adjuvant in compositions such as food products, cosmetics and pharmaceuticals which have activities to promote the growth of bifid bacteria and the mineral absorption, and to prevent caries.

EXAMPLE A-9

A reaction mixture containing α-isomaltosyl α-isomaltoside, obtained by the method in Example A-5, was in usual manner purified and concentrated into an about 50 w/v % syrup which was then, in accordance with the method in Example A-7, hydrogenated, purified and concentrated to obtain an about 70 w/v % syrup in a yield of about 80%, d.s.b. The product, containing about 18% α-isomaltosyl α-glucoside, about 4% α-isomaltosyl α-isomaltoside, about 5% α-isomaltotriosyl α-glucoside, d.s.b., and sugar alcohols, can be suitably used as a growth-promoting agent for bifid bacteria, mineral absorption-promoting agent, and anti-caries agent. The product has no reducibility but has a mild and high quality sweetness, and because of these it can be arbitrarily used as a sweetener, taste-improving agent, quality-improving agent, stabilizer, filler, excipient, adjuvant in compositions such as food products, cosmetics and pharmaceuticals which have activities to promote the growth of bifid bacteria and the mineral absorption, and to prevent caries.

EXAMPLE B-1

Sweetener

One part by weight of a powder of SACCHARIDES obtained by the method in Example A-2, 0.01 part by weight of "αG-SWEET", an α-glycosylstevioside product commercialized by Toyo Sugar Refining Co., Ltd., Tokyo, Japan, and 0.01 part by weight of "ASPARTAME" or L-aspartyl-L-phenylalanine methyl ester were mixed to homogeneity, and the mixture was granulated with a granulator to obtain a granular sweetener. The product, a composition with activities to promote the growth of bifid bacteria and the mineral absorption, can be suitably used as a food for beauty or health and as a sweetener for anti-caries foods because dental caries-inducing microorganisms form less acids and insoluble glucans in the presence of the product. The product has a high quality sweetness and an about 2.5-fold higher sweetening power of sucrose, and the calorific value per sweetening power is as low as about ½.₅ of that of sucrose. The product has a satisfactory stability without decomposition of the incorporated "αG-SWEET" and "ASPARTAME" as sweeteners with a high sweetening power and can be suitably used as a low caloric sweetener to sweeten low-caloric foods for fat persons and diabetics whose caloric intakes are restricted. In addition, the product less forms insoluble glucans so that it can be arbitrarily used to sweeten anti-caries foods.

EXAMPLE B-2

Hard candy

One hundred parts by weight of a 55 w/v % sucrose solution was mixed under heating conditions with 30 parts by weight of a syrup of SACCHARIDES obtained by the method in Example A-1, and the mixture was concentrated in vacuo by heating up to give a moisture content of less than 2%, admixed with one part by weight of citric acid and adequate amounts of a lemon flavor and a coloring agent, and shaped in usual manner into the desired product. The product is a composition with an activity to promote the growth of bifid bacteria or a hard candy with such an activity and a less dental caries-inducibility. The product is a high quality and low-cariogenic hard candy having a satisfactory biting property and taste and being free from sucrose crystallization.

EXAMPLE B-3

Chewing gum

Three parts by weight of a gum base was melted by heating until it softened, mixed with 3 parts by weight of a crystalline maltitol powder and 4 parts by weight of a powder of SACCHARIDES obtained by the method in Example A-8, and further mixed with adequate amounts of a flavoring agent and a coloring agent. The mixture was in usual manner kneaded by a roll, shaped and packed into the desired product. The product is a composition with an activity to promote bifid bacteria, i.e. a chewing gum which has such an activity, an insubstantial dental-caries inducibility, and a satisfactory texture and flavor.

EXAMPLE B-4

Vegetable juice

In 1,000 parts by weight of a vegetable juice consisting mainly of tomato juice were dissolved 10 parts by weight of a syrup of SACCHARIDES obtained by the method in Example A-9, and 5 parts by weight of pullulan having an average molecular weight of about 10,000, and the solution was in usual manner sterilized by heating and canned into the desired product. The product is a composition, which has activities to promote the growth of bifid bacteria and to prevent caries, can be suitably used as foods for beauty or health having such an activity and an activity to promote the mineral absorption because it contains, in addition to the saccharide which promotes the growth of bifid bacteria, vitamins and minerals from vegetables.

EXAMPLE B-5

Custard cream

One hundred parts by weight of corn starch, 100 parts by weight of a syrup of SACCHARIDES obtained by the method in Example A-3, 80 parts by weight of maltose, 20 parts by weight of sucrose, and one part by weight of salt were mixed sufficiently. The mixture was admixed and stirred with 280 parts by weight of eggs, admixed gradually with 1,000 parts by weight of a boiling milk, and heated under stirring conditions. The heating was stopped when the corn starch was completely gelatinized to show the whole contents semitransparent, then successively cooled, admixed with an adequate amount of a vanilla flavor, weighed, injected, and packaged to obtain the desired product. The product is a composition with activities to promote the growth of bifid bacteria and to prevent caries, and is suitably used as foods for beauty or heath having such activities and an activity to promote the mineral absorption. The product has a smooth surface and gloss, mild sweetness, and satisfactory taste.

EXAMPLE B-6

Uiro-no-moto

Ninety parts by weight of rice powder was mixed to homogeneity with 20 parts by weight of corn starch, 40 parts by weight of sucrose, 80 parts by weight of a powder of SACCHARIDES obtained by the method in Example A-4, and 4 parts by weight of pullulan to obtain the desired product. The product was kneaded with water and an adequate amount of matcha (a green tea), and the mixture was placed in a container and steamed up over 60 min to obtain a matcha uiro. The product is a composition with activities to promote the growth of bifid bacteria and to prevent caries, and can be suitably used as foods for beauty or health having such an activity. The product has a satisfactory gloss, biting property, and taste. Since the retrogradation of the starch is well inhibited, the product has a relatively-long shelf life.

EXAMPLE B-7

Sweetened condensed milk

Three parts by weight of a syrup of SACCHARIDES obtained by the method in Example A-7, and one part by weight of sucrose were dissolved in 100 parts by weight of raw milk, and the mixture was sterilized by heating on a plate heater, concentrated up to give a concentration of 70 w/v %, and canned aseptically to obtain the desired product. The product, having a mild sweetness and a satisfactory taste, can be arbitrarily used as a seasoning for foods directed to babies and infants, and for fruit, coffee, cocoa and tea. The product is a composition with activities to promote the growth of bifid bacteria and the mineral absorption and to prevent caries, and can be suitably used as foods for beauty or health having such an activity and an activity to promote the mineral absorption.

EXAMPLE B-8

Cosmetic cream

Two parts by weight of polyoxyethyleneglycoal monostearate, 5 parts by weight of glyceryl monostearate, selfemulsifying, 2 parts by weight of either of powdery SACCHARIDES obtained by the method in Experiment 1, one part by weight of α-glycosyl rutin, one part by weight of liquid paraffine, 10 parts by weight of glyceryl trioctanoate, and an adequate amount of an antiseptic were mixed by conventional manner. To the mixture were added 5 parts by weight of 1,3-butylene glycol and 66 parts by weight of refined water, and the resultant mixture was emulsified by a homogenizer, then admixed with an adequate amount of a flavor to obtain the desired product. The product with a satisfactory stability can be arbitrarily used a high-quality sun screening, skin beautifying, and skin whitening.

Example B-9

Solid preparation

A natural human interferon-α specimen produced by Hayashibara Biochemical Laboratories, Inc., Okayama, Japan, was in usual manner subjected to a column of an immobilized anti-human interferon-α antibody to adsorb the human interferon-α, followed by passing through a calf serum albumin as a stabilizer and removing an excessive amount of the serum. Thereafter, the human interferon-α was eluted from the column by feeding to the column with a physiological saline containing 5% of either of powdery SACCHARIDES obtained by the method in Experiment 1 while changing the pH. The eluate was membrane filtered, dehydrated by the addition of about 20-fold volumes of "FINETOSE®" an anhydrous crystalline maltose powder commercialized by Hayashibara Co., Ltd., Okayama, Japan, into a powdery product which was then tabletted by a tabletting machine into tablets, containing about 150 units of the human interferon-α per tablet, 200 mg weight. The tablet is used orally as a sublingual agent at a dose of about 1–10 tablets/day/adult for the treatment of viral diseases, allergies, rheumatisms, diabetics and malignant tumors. Particularly, the tablet can be suitably used as a therapeutic agent to treat patients suffering from AIDS and hepatitis, the number of which has been increasing. The tablet has a relatively-long shelf life even when stored at ambient temperature because maltose and α-isomaltosyl α-glucoside, α-isomaltosyl α-isomaltoside and/or α-isomaltotriosyl α-glucoside in the tablet act as a stabilizer for the human interferon-α.

EXAMPLE B-10

Tablet

Twenty parts by weight of a powder of SACCHARIDES obtained by the method in Example A-2, 30 parts by weight of hydrous crystalline trehalose, one part by weight of calcium lactate, one part by weight of sugar ester, and an adequate amount of a powdery flavor were mixed to homogeneity, and the mixture was in usual manner tabletted with a tabletting machine to obtain tablets, about 350 mg weight each. The product is a composition with activities to promote the growth of bifid bacteria and to prevent caries, and can be suitably used as foods for beauty or health having such an activity and an activity to promote the calcium absorption. The cracking is well prevented and is satisfactorily stable and readily swallowable so that it can be administered usually at a dose of about 1–40 tablets/day/adult, preferably, about 2–20 tablets/day/adult.

EXAMPLE B-11

Tablet

Twenty parts by weight of a power of SACCHARIDES obtained by the method in Example A-4, 10 parts by weight of "NYUKA ORIGO®", a lactosucrose powder commercialized by Hayashibara Shoji, Inc., Okayama, Japan, 20 parts by weight of lactose, one part by weight of calcium tertiary phosphate, one part by weight of calcium lactate, one part by weight of sugar ester, and adequate amounts of a powdery edible coloring agent and an edible flavor were mixed to homogeneity. The mixture was in usual manner tabletted by a tabletting machine to obtain tablets, about 680 mg weight each. The product is a composition with activities to promote the growth of bifid bacteria and to prevent caries, and can be suitably used as foods for beauty or heath which have both activities to promote the growth of bifid bacteria and the calcium absorption. In use, the product is administered at a dose of about 1–40 tablets/day/adult, preferably, about 2–20 tablets/day/adult.

Example B-12

Nutrition

A composition, consisting of 480 parts by weight of anhydrous crystalline maltose, 190 parts by weight of dried eggs, 209 parts by weight of a skim milk powder, 115 parts by weight of a powder of SACCHARIDES obtained by the method in Example A-2, 4.4 parts by weight of sodium chloride, 1.85 parts by weight of potassium chloride, 4 parts by weight of magnesium sulfate, 0.01 part by weight of thiamine, 0.1 part by weight of sodium ascorbate, 0.6 parts by weight of vitamin E acetate, and 0.04 parts by weight of nicotinic acid amide, was prepared. Twenty-five g aliquots of the composition were injected into laminated-aluminum small bags and heat sealed to obtain nutrients which are dissolved in solvents before use. The product, having a satisfactory solubility and dispersibility, requires no cold storage and has a relatively-long shelf life even at ambient temperature. The product is a composition with activities to promote the growth of bifid bacteria and to prevent caries. In use, one bag of the product is administered to nasal caries, throat and stomach by an intubation feeding after dissolved in about 150–300 ml hot water, followed by acting as a nutritional supplement, promoting the growth of bifid bacteria and the mineral absorption to recover the heath of patients suffering from diseases. Particularly, the product promotes the growth of bifid bacteria in the large intestines, lowers the pH, and inhibits the production of harmful substances by putrefactive bacteria. Furthermore, the product increases the feces' amount and prevents the constipation usually occurring in the patients. Needless to say, the product can be arbitrarily used as a composition with an activity to promote the growth of bifid bacterial which is administrable to domestic animals orally or in an intubation manner.

EXAMPLE B-13

Nutrition

A composition, consisting of 14.5 parts by weight of anhydrous crystalline trehalose, 4.05 parts by weight of sucrose, 3.2 parts by weight of a powder of mandarin orange juice, 3.0 parts by weight of a powder of SACCHARIDES obtained by the method in Example A-5, 0.11 parts by weight of citric acid, 0.02 parts by weight of L-ascorbic acid, and 0.1 part by weight of a powdery orange juice, was prepared. Four hundred g aliquots of the composition were injected into cans with screw caps and sealed to obtain the desired product, a type of which is used by dissolving in a solvent before use. Similarly as the product in Example B-10, the product has a satisfactory stability and solubility, and an activity to promote the growth of bifid bacteria. In use, about 25 g of the product is first dissolved in about 100–150 ml hot water, then administered orally or in an intubation manner to supplement nutrition and to promote the growth of bifid bacteria and the mineral absorption, resulting in the recovery of health of patients suffering from diseases. Also the product can be arbitrarily used as a nutrition which the sucrose cariogenicity is well inhibited.

EXAMPLE B-14

Assorted feed

An assorted feed was obtained by mixing 40 parts by weight of powdery bran, 38 parts by weight of skim milk powder, 12 parts by weight of a powder of SACCHARIDES obtained by the method in Example A-5, 10 parts by weight of a vitamin agent, 5 parts by weight of fish flour, 5 parts by weight of calcium secondary phosphate, 3 parts by weight of liquid oils and fats, 3 parts by weight of calcium carbonate, 2 parts by weight of salt, and 2 parts by weight of a mineral agent. The product is a feed with an improved taste preference for domestic animals and poultry, and can be specifically used for infant pigs. The product has an activity to promote the growth of bifid bacteria and exerts activities to promote the growth of bifid bacteria and the mineral absorption. Furthermore, the product can be arbitrarily used to prevent such animals from infectious diseases and diarrhea, promote their appetite, and inhibit unsatisfactory smell of their feces. If necessary, the product can be prepared into other types of feeds by mixing with materials for concentrates such as crops, wheat flours, starches, oil meals, and rice-bran saccharides, as well as crude feeds such as straws, hays, bagasses and corncobs.

EXAMPLE B-15

Toothpaste

Forty-five parts by weight of calcium secondary phosphate, 2.95 parts by weight of pullulan, 1.5 parts by weight of sodium lauryl sulfate, 20 parts by weight of glycerine, 0.5 parts by weight of polyoxyethylene sorbitan laurate, 0.05 parts by weight of an antiseptic, 15 parts by weight of a syrup of SACCHARIDES, 5 parts by weight of sucrose, and 10 parts by weight of water were mixed by conventional manner to obtain the desired product. Since the product has an appropriate sweetness, it is suitably used for infants.

As is described above, the SACCHARIDES, i.e. α-isomaltosyl α-glucoside, α-isomaltosyl α-isomaltoside and α-isomaltotriosyl α-glucoside as the present effective ingredients are stable in themselves and have a satisfactorily-high quality and mild sweetness. Although these saccharides are partly assimilated and used as an energy source when orally taken, most of them reach up to the large intestines and can be suitably used as a selective growth-promoting agent for bifid bacteria. When assimilated by bifid bacteria, these saccharides form organic acids which lower the pH in the large intestines, increase the solubility and absorption of minerals such as calcium and iron susceptible to defect. Furthermore, these saccharides are not readily fermented by dental caries-inducing microorganisms so that they satisfactorily inhibit the formation of insoluble glucans from sucrose by such microorganisms, the plaque formation, and the induction of caries.

The SACCHARIDES, non-reducing saccharides, are chemically stable and capable of stabilizing biologically active substances susceptible to loss of their effective ingredients and activities. In addition, the SACCHARIDES have properties of an osmosis-pressure regulatory activity, filler-imparting activity, gloss-imparting activity, moisture-retaining activity, satisfactory viscosity, and crystallization-preventing activity for other saccharides, insubstantial fermentability, and retrogradation-preventing activity for starches. These properties are well applicable to produce a variety of compositions such as food products, feeds, pet foods, and pharmaceuticals which have activities to promote the growth of bifid bacteria and to prevent caries. These compositions have activities to promote the growth of bifid bacteria, the mineral absorption, and the inhibition of dental caries, and can be suitably used as foods for beauty or health.

Thus the present invention provides a great industrial significance in the fields of foods, cosmetics and pharmaceuticals.

While there has been described what is at present considered to be the preferred embodiments of the invention, it will be understood the various modifications may be made therein, and it is intended to cover in the appended claims all such modifications as fall within the true spirit and scope of the invention.

We claim:

1. α-Isomaltosyl α-isomaltoside represented by O-α-D-glucopyranosyl -(1→6)-α-D-glucopyranosyl-O-α-D-glucopyranosyl-(1→6)-α-D-glucopyranoside.

2. The α-isomaltosyl α-isomaltoside of claim 1, which has the physicochemical properties of:

(1) Elemental analysis Found: C=42.1%, H=6.3%, O=51.6% Theoretical value: C=41.98%, H=6.17%, O=51.85% (Chemical formula: $C_{24}H_{42}O_{21}$);

(2) Molecular weight 666.6 Daltons;

(3) Ultraviolet ray absorption Exhibiting no characteristic absorption when measured after dissolving in water;

(4) Taste Exhibiting about ⅕ sweetening power of sucrose, and having a satisfactory taste and no unfavorable smell;

(5) Solubility in solvent Readily soluble in water, 0.1N NaOH and 0.1N HCl. Hardly soluble in methanol and ethanol. Insoluble in chloroform and ethyl acetate;

(6) Coloring reaction Exhibiting green on the anthrone-sulfonic acid reaction. Negative on the Fehling reaction and the iodine reaction;

(7) Structure
      (a) Only forming D-glucose residues when hydrolyzed with 1N sulfuric acid;
      (b) Analysis of methylhexytolacetate on gas chromatography revealed that 1,5-di-O-acetyl-2,3,4,6-tetra-O-methylglucitol and 1,5,6-tri-O-acetyl-2,3,4-tri-O-methylglucitol are formed in a molar ratio of 1:1 after successive methylation, hydrolysis with an acid, reduction, and acetylation into glycitolacetate or methylhexytolacetate;
      (c) Being partially hydrolyzed by glucoamylase into glucose, trehalose and α-isomaltosyl α-glucoside but not hydrolyzed by isomaltodextranase; and
      (d) Giving 12 $^{13}C$ signals on $^{13}C$-NMR (nuclear magnetic resonance).

3. A composition which comprises a carrier and at least one member selected from the group consisting of α-isomaltosyl α-isomaltoside and α-isomaltotriosyl α-glucoside as an effective ingredient.

4. The composition of claim 3, wherein said α-isomaltosyl α-isomaltoside and α-isomaltotriosyl α-glucoside are prepared by allowing α-glucosidase together with or without α-glucoamylase to act on an aqueous solution containing trehalose and an amylaceous substance.

5. The composition of claim 4, wherein said aqueous solution is a mixture of an amylaceous substance and trehalose which is obtainable either by allowing a non-reducing saccharide-forming enzyme and a trehalose-releasing enzyme to act on an aqueous solution containing an amylaceous substance or allowing a maltose/trehalose converting enzyme to act on an aqueous solution containing maltose or an aqueous solution containing a compound having a trehalose structure and an amylaceous structure of an α-1,4 glucosidic linkage within the molecule, said compound being obtainable by allowing a non-reducing saccharide-forming enzyme together with or without cyclomaltodextrin glucanotransferase to act on an aqueous solution containing an amylaceous substance.

6. The composition of claim 3, which comprises one or more members selected from the group consisting of α-isomaltosyl α-isomaltoside and α-isomaltotriosyl α-glucoside along with one or more members selected from the group consisting of α-isomaltosyl α-glucoside, sugar alcohols, minerals and sucrose.

7. The composition of claim 3, which is in the form of an orally administrable product, food, cosmetic or pharmaceutical.

8. The composition of claim 3, which is a growth-promoting agent for bifid bacteria.

9. The composition of claim 3, which is a mineral absorption-promoting agent.

10. The composition of claim 3, which is an anti-carries agent.

11. The composition of claim 10, which contains sucrose and the amount of said effective ingredient is at least 5.0 w/w % to said sucrose, on a dry solid basis.

12. The composition of claim 3, wherein said effective ingredient is incorporated thereunto in an amount of at least 0.1 w/w %, on a dry solid basis.

* * * * *